(12) United States Patent
Lanois et al.

(10) Patent No.: US 9,241,705 B2
(45) Date of Patent: *Jan. 26, 2016

(54) BONE ANCHOR DELIVERY SYSTEM DEVICE WITH SUTURES

(71) Applicant: Valeris Medical, LLC, Woodstock, GA (US)

(72) Inventors: Daniel Brian Lanois, Atlanta, GA (US); Bradford Lee Boone, Tulsa, OK (US); Ryan Eric Gursky, Tulsa, OK (US); James Calvin Johnson, Oklahoma City, OK (US); Bruce Scott Markman, Bixby, OK (US)

(73) Assignee: Valeris Medical, LLC, Marietta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/677,204

(22) Filed: Apr. 2, 2015

(65) Prior Publication Data

US 2015/0216524 A1 Aug. 6, 2015

Related U.S. Application Data

(63) Continuation of application No. 14/572,199, filed on Dec. 16, 2014.

(60) Provisional application No. 61/928,095, filed on Jan. 16, 2014.

(51) Int. Cl.
*A61B 17/04* (2006.01)
*A61B 17/88* (2006.01)

(52) U.S. Cl.
CPC ......... *A61B 17/0401* (2013.01); *A61B 17/8875* (2013.01); *A61B 17/8877* (2013.01); *A61B 2017/044* (2013.01); *A61B 2017/0409* (2013.01); *A61B 2017/0414* (2013.01); *A61B 2017/0445* (2013.01)

(58) Field of Classification Search
CPC ................. A61B 2017/0495; A61B 2017/044; A61B 2017/0414; A61B 2017/0456; A61B 2017/0458; A61B 2017/0453; A61B 2017/0446; A61B 2017/0441; A61B 2017/0445; A61B 2017/0409; A61B 2017/041
USPC ......................................... 606/232
See application file for complete search history.

(56) References Cited

U.S. PATENT DOCUMENTS

| | | | |
|---|---|---|---|
| 6,045,573 A * | 4/2000 | Wenstrom et al. | 606/232 |
| 6,544,281 B2 | 4/2003 | Elattrache et al. | |
| 7,329,272 B2 | 2/2008 | Burkhart et al. | |
| 7,585,311 B2 | 9/2009 | Green et al. | |
| 7,993,369 B2 | 8/2011 | Dreyfuss | |
| 8,114,127 B2 | 2/2012 | West | |
| 8,430,909 B2 | 4/2013 | Dreyfuss | |
| 8,663,279 B2 | 3/2014 | Burkhart et al. | |
| 2012/0150226 A1 | 6/2012 | Burkhart | |
| 2013/0253581 A1* | 9/2013 | Robison | 606/232 |

* cited by examiner

*Primary Examiner* — Kathleen Holwerda
*Assistant Examiner* — Socrates L Boutsikaris
(74) *Attorney, Agent, or Firm* — David L. King (57) ABSTRACT

The device (10) has a handle assembly (40) and a bone anchor driver assembly (20). The handle assembly (40) has an upper handle portion (50) and a lower handle portion (60). The upper or lower handle portion is rotatable relative to the other handle portion. A bone anchor driver assembly (20) is for rotatably driving a bone anchor (12) into a hole in a bone. The bone anchor driver assembly (20) is fixed to one of either the upper or lower handle portions (50 or 60).

11 Claims, 7 Drawing Sheets

BONE ANCHOR DELIVERY SYSTEM DEVICE WITH SUTURES

RELATED APPLICATIONS

The present application is a continuation of co-pending U.S. application Ser. No. 14/572,199 filed Dec. 16, 2014 entitled "Bone Anchor Delivery System Device With Sutures".

TECHNICAL FIELD

The present invention relates to methods and instruments for fixation of sutures and tissue to bone, more particularly to a bone anchor system for securing sutures for attachment of soft tissue like ligament and cartilage to bone.

BACKGROUND OF THE INVENTION

The use of bone screw anchors to hold sutures is a widely accepted practice in shoulder or knee repair and fixation of soft tissue such as ligaments, cartilage and tendons to bone. Ideally the suture anchor is easy to install and provides a solid reliable way to fix the sutures to the bone. The bone has a hard outer cortical shell with a softer underlying region of cancellous bone tissue. The anchor must hold sutures after thousands of repetitive motions tensioning and relaxation until the ligament or tendon repair has time to heal and secure itself to the bone and muscle tissue.

Older style bone anchors had an external eyelet to allow the sutures to be fed through after the screw was driven into the bone. This left the eyelet exposed in the soft muscle tissue.

Later versions of bone anchors have the sutures inserted inside the screw tip well inside the bone. This allows the screw outer end to stay flush with the cortical bone outer surface. The sutures can pass inside in some hollow screws from the tip to the outer surface. A main problem is how to thread the bone anchor into the bone. In some suture anchor systems there is a self-driving feature that has a punch tip that can be malleted into the bone. Once started, the anchor must be rotated to thread it into the bone. The ends of the sutures are often dangling in the way.

Ideally the procedure should insure the bone anchor is easily installed without having the sutures interfering with the anchoring.

The present invention provides a threaded bone anchor that is easy to install wherein the sutures are held securely with the bone anchor, but wherein the ends of the sutures are contained inside the delivery device.

SUMMARY OF THE INVENTION

A bone anchor delivery system device has a handle assembly and a bone anchor driver assembly. The handle assembly has an upper handle portion and a lower handle portion. The upper and lower handle portions are rotatable relative to the other. The bone anchor driver assembly provides for rotatably driving a bone anchor. The bone anchor driver assembly is fixed to one of said upper or lower handle portions. The handle assembly rotation of one of the handle portions is fixed to the driver allowing the other handle portion to be held non-rotatably for stabilization of the device. Preferably, the upper handle portion is fixed to the driver assembly. The upper handle portion also has an impact end for receiving blows from a mallet and the driver assembly has a leading end to which is attached a removable bone anchor with a punch or tapered end for penetrating bone to form an anchor opening. The bone anchor delivery system device has the bone anchor releasable relative to the driver assembly. The bone anchor driver assembly further non-rotatably holds the bone anchor, said bone anchor being releasably held on said driver assembly, and wherein after being driven into said anchor opening, the driver assembly is withdrawn releasing said bone anchor fixed to said bone opening. In the preferred embodiment, the bone anchor has suture threads attached that are rotatably driven into the bone opening with the bone anchor.

In the preferred embodiment, the bone anchor driver assembly includes an elongated drive shaft fixed to the handle, the drive shaft having a hollow stem extending from the handle to the leading end. The bone anchor driver assembly drive shaft has the leading end with a tip portion extending from the leading end. The tip portion has a pair of openings for receiving sutures and at least one flat surface extending along the tip portion lengthwise to rotationally fix the bone anchor to the drive shaft.

The bone anchor has a hollow end for receiving and being removably attached on said tip portion. The bone anchor has at least one pair of suture openings, each pair of suture openings being within a thread channel formed by two adjacent threads. The two openings of each pair are within 90 degrees of the other and extending into the hollow end opening. The bone anchor delivery system device further has a suture threaded and looped through the at least one pair of suture openings, the suture extending from the bone anchor through one of the tip openings internally through the hollow stem of the drive shaft of the bone anchor driver assembly.

The bone anchor delivery system device has a second pair of openings for receiving a second suture. The second pair is within a thread channel formed by two adjacent threads being similarly spaced relative to the first pair, but on opposite sides of the bone anchor, and a second suture threaded through the second pair of openings and similarly extending through the tip and the stem of the drive shaft. The bone anchor delivery system device has only a very short loop portion of each the sutures exposed externally in the thread channel. The exposed looped portion extends at 90 degrees or less circumferentially around the channel from the pair of openings in which the suture is held to the bone anchor. Each pair of the suture ends of the first or second suture extend along only one side of the bone anchor through one opening on the tip to the stem, wherein all four suture ends extend to the handle and are wrapped around a recess groove in an end portion of the handle. The bone anchor delivery system device further has a removable cover wherein said recess groove holds the suture ends and the removable cover encircles the sutures ends wrapped in said groove. The removable cover can be an elastomeric O ring.

The bone anchor can have two or more pairs of suture openings with each opening of one pair radially or linearly aligned or radially or linearly offset relative to the openings of another pair.

DEFINITIONS

As used in this specification, the singular forms "a," "an" and "the" include plural referents unless the context clearly dictates otherwise. Thus, for example, the term "a material" is intended to mean one or more materials, or a combination thereof.

BRIEF DESCRIPTION OF THE DRAWINGS

The invention will be described by way of example and with reference to the accompanying drawings in which.

DETAILED DESCRIPTION OF THE INVENTION

Figure 1:
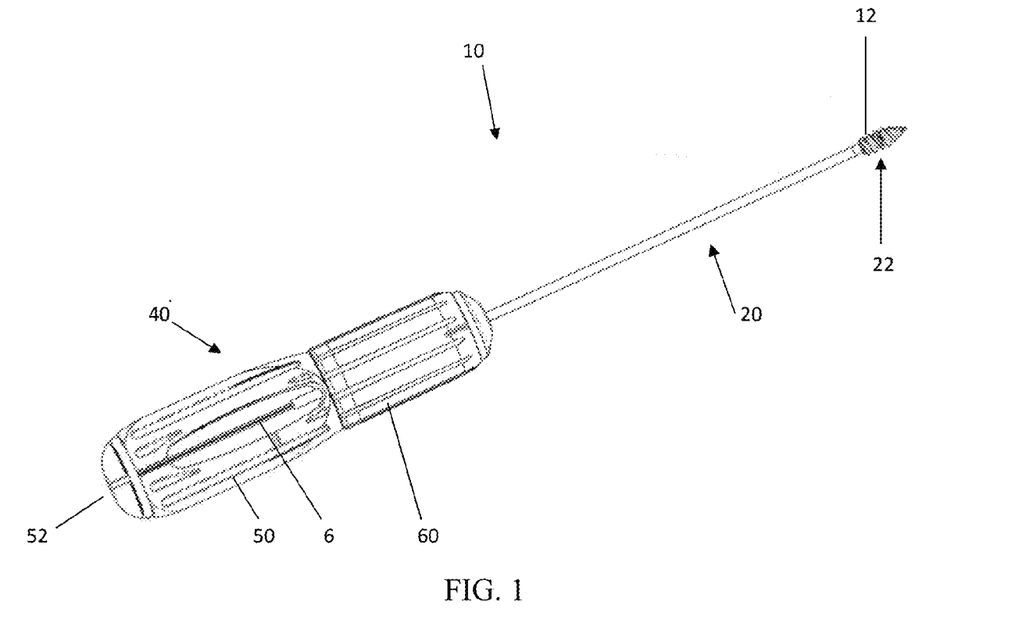
FIG. 1 is a perspective view of the bone anchor delivery system device according to the present invention.

With reference to FIG. 1, a perspective view of the bone anchor delivery system device 10 is shown. The device 10 has a handle assembly 40 and a bone anchor driver assembly 20. The handle assembly 40 has an upper handle portion 50 and a lower handle portion 60 as illustrated. The upper or lower handle portion is rotatable relative to the other handle portion. A bone anchor driver assembly 20 is for rotatably driving a bone anchor 12 into a hole in a bone is provided. The bone anchor driver assembly 20 is fixed to one of either the upper or lower handle portions 50 or 60. As shown, the bone anchor driver assembly 20 is fixed to the upper handle portion 50 in the illustrated embodiment. Alternatively, it could be fixed to the lower handle portion 60, if so desired. The handle assembly 40 during rotation of the handle portion fixed to the driver assembly 20 allows the other handle portion to be held non-rotatably to stabilize the device 10 during insertion of the bone anchor 12. The upper handle portion 50 preferably has an impact end 52 for receiving blows from a mallet and the driver assembly 20 has a leading end or tip portion 22 having a removable bone anchor 12 with a punch tip 14 with a tip portion 22 positioned on a sharpened metal pointed tip 25 for penetrating bone to form the anchor opening. The bone anchor 12 preferably is releasable relative to the driver assembly 20. As shown, the bone anchor driver assembly 20 non-rotatably holds the bone anchor 12. This is accomplished by providing a flat 23 at the leading end or tip portion 22 of a drive shaft 21 included as part of the driver assembly 20, as shown in FIG. 4A. When the bone anchor 12 is driven into said bone anchor opening, the driver assembly 20 is withdrawn releasing the bone anchor 12 fixed to the bone opening. The bone anchor 12 preferably has suture threads attached that are rotatably driven into the bone opening via the driver shaft 21.

Figure 2:
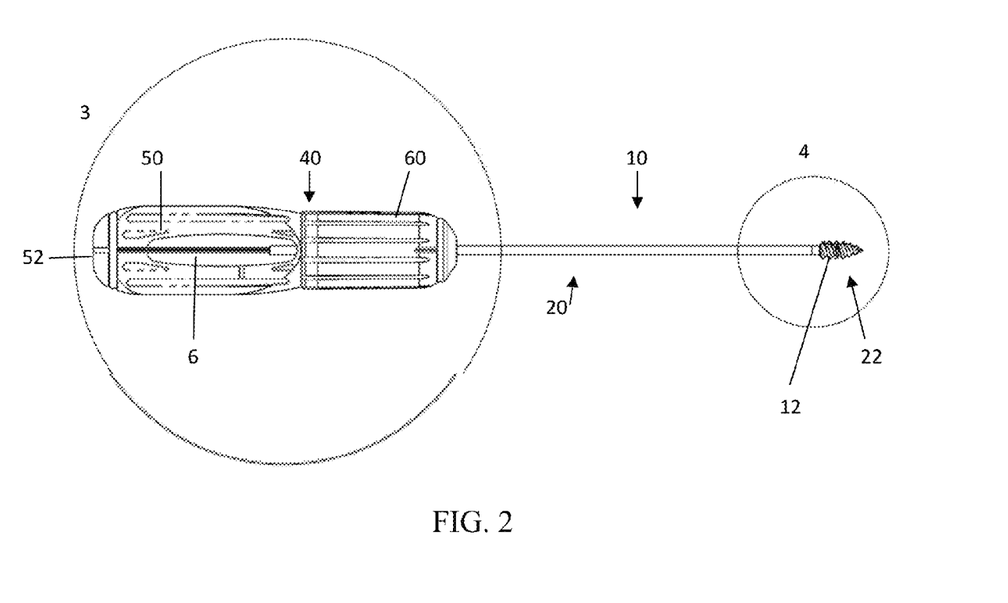
FIG. 2 is a side plan view of the device of FIG. 1.
Figure 3:
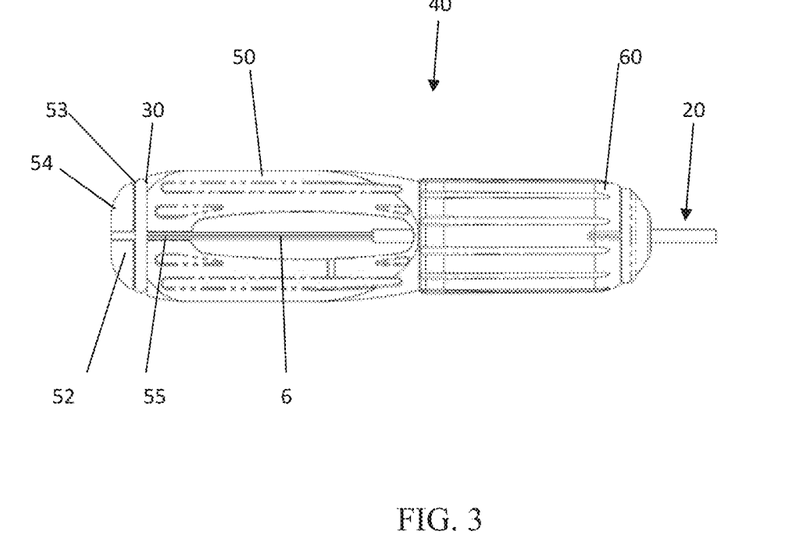
FIG. 3 is an enlarged view of the handle portion.
Figure 4:
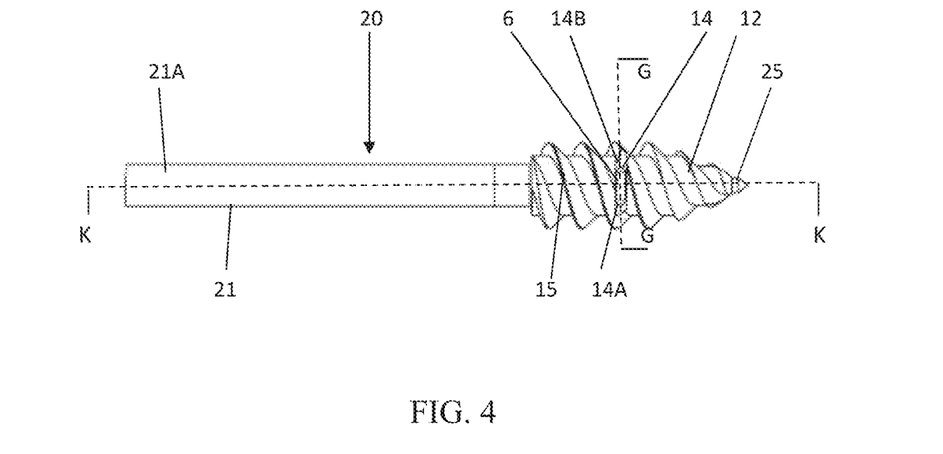
FIG. 4 is a view of the leading end of the drive assembly showing the tip portion for receiving a bone anchor.
Figure 4A:
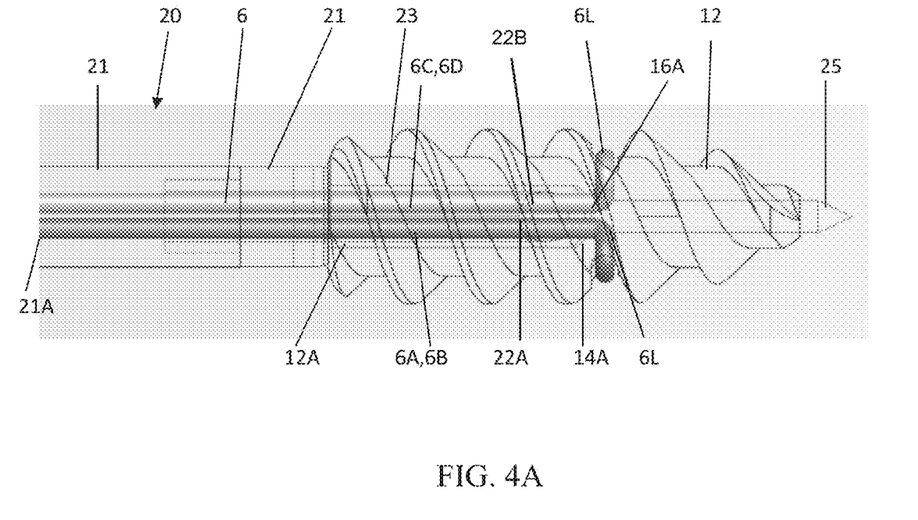
FIG. 4A is an enlarged side view of the tip portion showing the anchor in phantom.
Figure 4B:
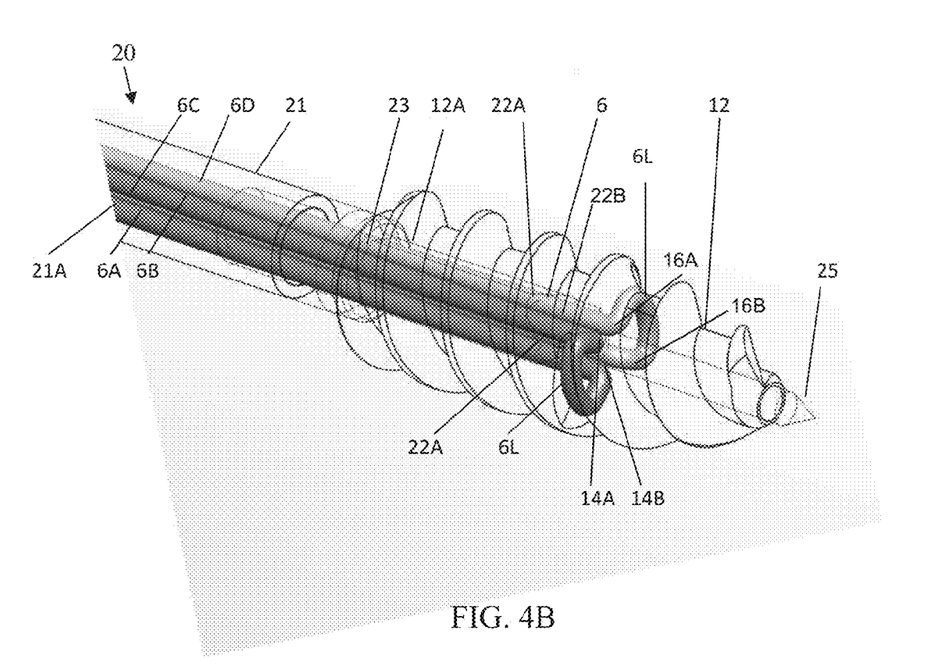
FIG. 4B is a perspective view of FIG. 4A.
Figure 4C:
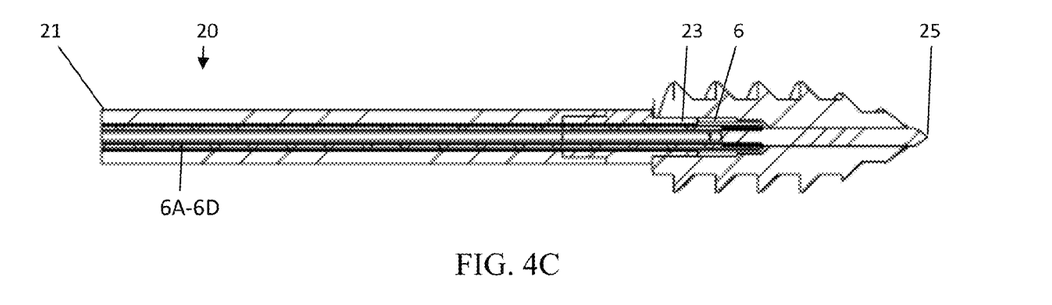
FIG. 4C is a cross sectional view taken along lines K-K of FIG. 4.

With reference to FIG. 4, a side or plan view is shown at the anchor 12 end of the device 10. In the preferred embodiment, the device 10 has the bone anchor 12 having at least one pair 14 of holes 14A, 14B; as shown in FIGS. 4A-4D, two pairs 14, 16 having holes 14A, 14B and 16A, 16B. These holes 14A, 14B are in a channel 13 between two adjacent threads 15 and extend circumferentially 90 degrees or less within the channel 13 so that the openings 14A and 14B are both on one side of the screw threads 15 of the bone anchor 12 and openings 16A, 16B within the other pair 16 are within an opening side of the screw threads 15 of the bone anchor 12. As further illustrated, in FIG. 2, suture 6 can be looped through the openings 14A, 14B such that both ends 6A, 6B of the suture 6 extend through a hollow opening 12A in the anchor 12. The bone anchor 12 is illustrated in the perspective view of FIG. 5. These sutures 6 extend through the openings 14A, 14B into the hollow opening 12A in the bone anchor 12 that is adapted to fit onto the tip portion 22 of the leading end of the drive shaft 21. The sutures 6 extend through the anchor openings 14A, 14B and 16A, 16B into opening 12A and into openings 22A in the leading end tip portion 22. These openings 22A are for receiving the sutures 6. The tip portion 22 further has at least one flat surface 23 extending along the tip 22 lengthwise to rotationally fix the bone anchor 12 to the drive shaft 21. The sutures 6 when positioned into the pair of openings 14, 16 within the channel 13 form a loop 6L that are externally exposed only within a very short region within one pair of threads 15 such that the exposed portion extends less than 90 degrees around the circumference of the bone anchor channel 13. Both ends 6A, 6B of the sutures 6 are then fed through one of the openings 22A in the tip 22 and extend up a hollow stem opening 21A of the drive shaft 21 upwards and through the drive shaft 21 which is fixed to the upper handle portion 50 as illustrated. The sutures 6 extend through a vertical slot 55 to an end 52 of the handle assembly 40. The end 52 of the handle portion has a recessed groove 53 between the impact end surface 54 of the end 52 of the upper handle portion 50. It is in this recessed groove 53 that the sutures 6 extend upward through the vertical slot 55 and are wrapped about the recessed groove 53 several times thereby positioning the sutures 6 in such a fashion that they are completely internal of the device 10 within the handle assembly 40. Preferably, the suture ends 6A, 6B are then covered by a cover 30 that is preferably elastomeric stretching over the sutures 6 and holding them in place. As shown, the cover 30 is an O Ring 30 adapted to fit in the recessed groove 53 and hold the sutures 6A, 6B ends in place. The bone anchor 12 can have two or more pairs of suture openings 14, 16 with each opening of one pair radially or linearly aligned or radially or linearly offset relative to the openings of another pair.

With respect to FIGS. 1, 2 and 4A-4D, the bone anchor driver assembly 20 by having an elongated drive shaft 21 affixed to the handle assembly 40 has a long hollow stem opening 21A can accommodate a substantial length of sutures 6. Preferably, the second pair 16 of openings 16A, 16B on the bone anchor 12 are provided in an opposite side channel 13. The two pairs of openings 14, 16 again extend into the hollow end 12A of the bone anchor 12 such that a second pair of sutures 6 can be looped through the openings 16A, 16B into the hollow ends 12A of the bone anchor 12 extend through a second opening 22B in the tip 22 and extending up through the hollow stem opening 21A of the drive shaft 21. These sutures 6 having ends 6C, 6D can be used in combination with the other suture ends 6A, 6B so that four threads of suture 6 extend through the handle assembly 40 and are wrapped in the recessed groove 53 as previously discussed.

As illustrated in FIGS. 6A-6D, on insertion of the bone anchor 12 into a bone, the surgeon will take the device 10, find the position in which he wants to pierce the bone 2 creating a bone opening 3 and then take a mallet and impact the end surface 54 of the device such that the bone anchor 12 penetrates and initiates the hole 3 deeper into the inner bone tissue 4. Once the hole 3 is initiated, the bone anchor 12 can then be rotatably threaded into the bone opening 3 until the top of the bone anchor 12 is flush with the bone 2. When this occurs, the surgeon can simply pull the device 10 off of the leading end tip portion 22 leaving it in the bone opening 3 and the sutures 6 can then be pulled through the device 10 and left exposed out of the end of the bone anchor 12. In this fashion, the surgeon can manipulate the entire device 10 by holding one of the lower non-rotating handle portion 60 as he rotates the upper handle portion 50 to rotate the fixed drive shaft 21 and drive the bone anchor 12 into the bone opening 3. This is accomplished with only a very small portion of the suture 6 being exposed at the loops 6L which is only exposed within one pitch of the thread 15 within a distance occupying less than 90 degrees around the circumference of the channel 13 formed between the two adjacent threads 15. The suture opening pairs 14, 16 by being provided in pairs on each side of the bone anchor 12 provide secure sets of suture ends 6A-6D that can attach ligament or other soft tissue during a bone or knee, shoulder repair.

Figure 4D:
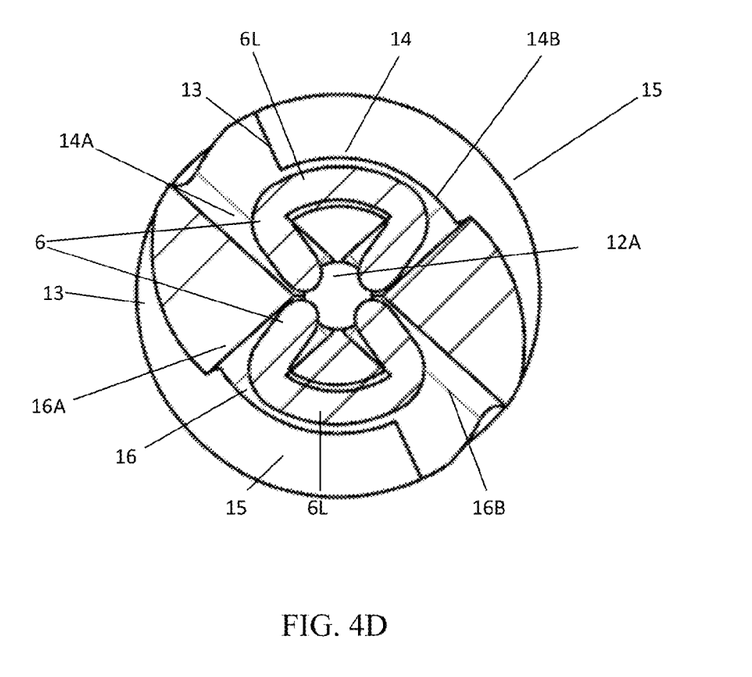
FIG. 4D is an end view taken along lines G-G of FIG. 4.
Figure 5:
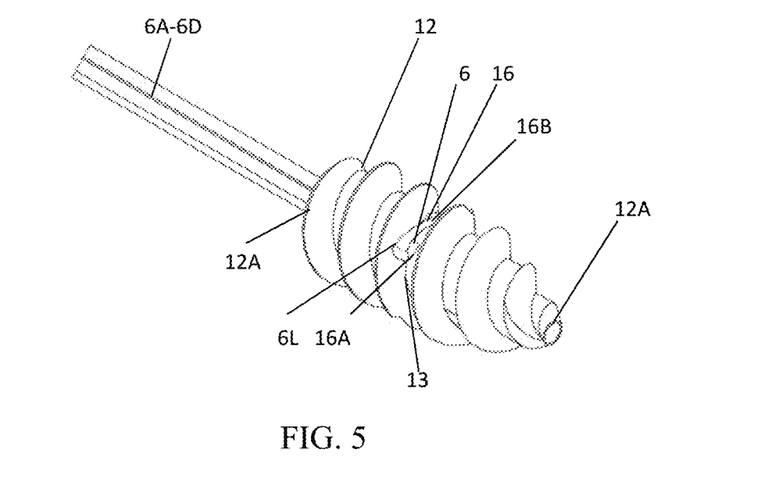
FIG. 5 is a perspective view of the bone anchor showing the sutures.
Figure 6A:
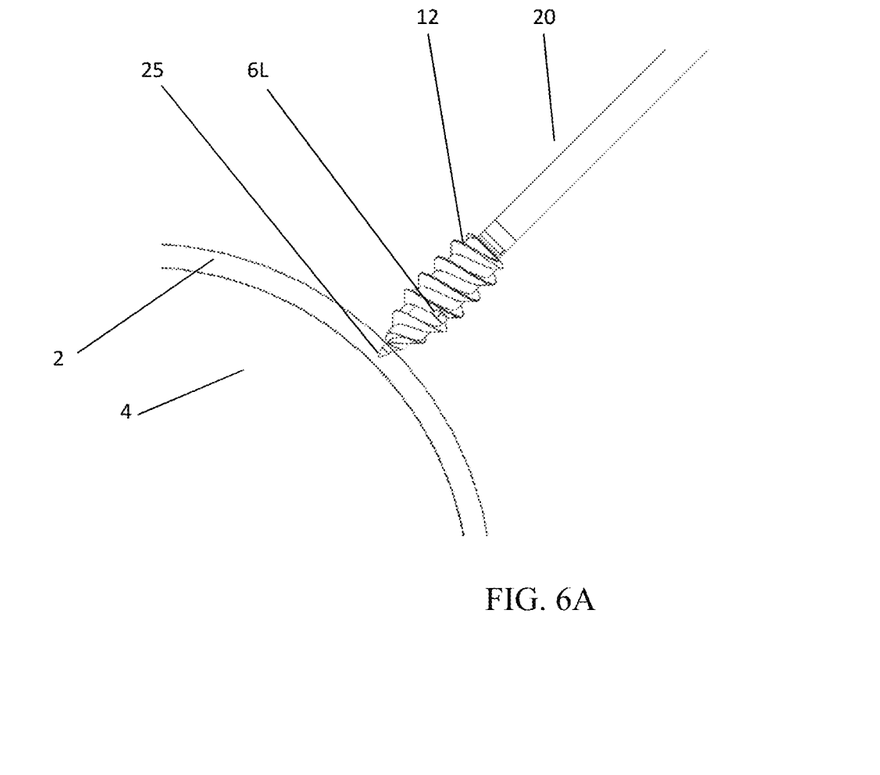
FIGS. 6A-6D show the preferred procedure or method of using the device of the present invention.
Figure 6B:
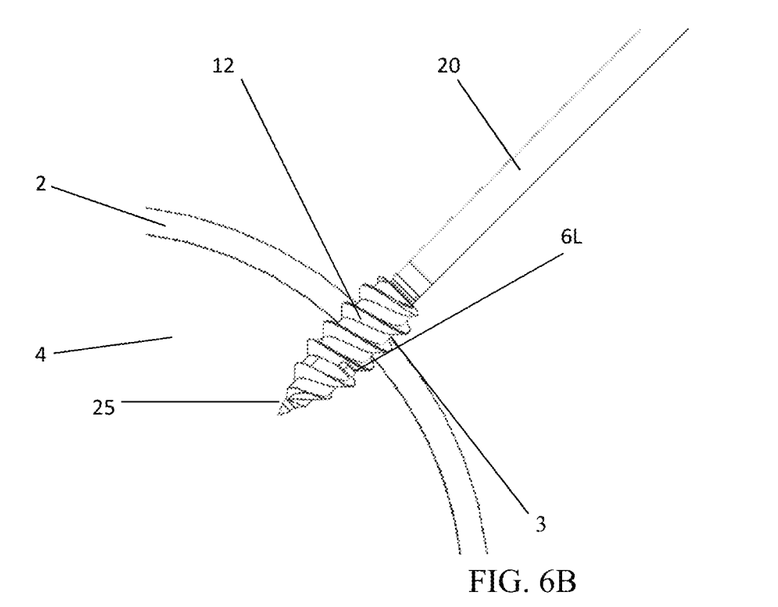
Figure 6C:
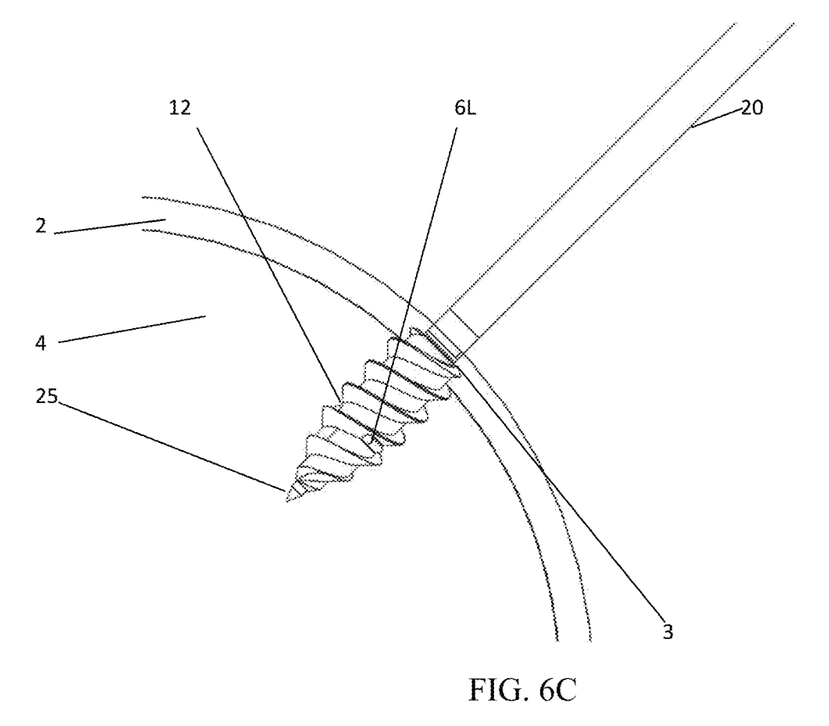
Figure 6D:
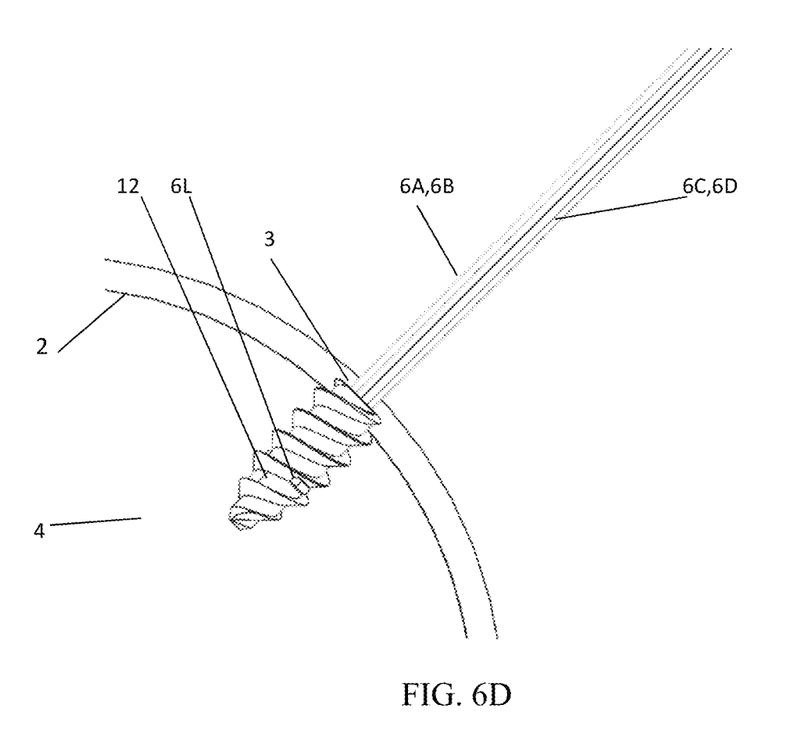

As further illustrated in FIGS. 4-4D, in the preferred embodiment, the bone anchor 12 actually has a hollow opening 12A extending all the way through the bone anchor 12 and the drive shaft 21 includes a sharpened metal pointed tip 25 and extending partially through the bone anchor 12. This is believed important in that it helps to locate the device 10 relative to the opening 3 to be made and provides a secure metal penetrating punch tip 25 to assist the bone anchor 12 during its insertion and forming of the bone hole opening 3. As illustrated, by applying pressure on the handle assembly 40, the bone anchor 12 can then be pressed into the bone 2 as it is being rotated, thereby creating a very tight compression fit. Due to the fact that the sutures 6 are only exposed over a short area, it is important to note that sutures 6 will be held in place and not pulled or cut by any threads 15 of the anchor 12 because the exposed loops 6L do not extend over any of the external portions of the threads 15, but are rather held within a tight constrained area within a single channel 13 on each side of the bone anchor 12. By having the sutures 6 contained almost entirely except for the loops 6L within the bone anchor delivery device 10, there are no suture ends or other suture threads that are exposed external of the device 10 until the device 10 is pulled from the bone anchor 12. Once this occurs, long lengths of sutures are provided from each pair of openings 14, 16. These sutures 6 will be used to tie off any soft tissue, ligaments or cartilage that are being attached to the bone. In this fashion, the delivery system device 10 creates a very simple and efficient way in which the sutures 6 can be secured internally of the bone anchor 12 without creating any cumbersome knotting or loops that could interfere with threads or the holding of the bone anchor 12.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A bone anchor delivery system device comprises:
    a handle;
    an elongated drive shaft fixed to the handle, the drive shaft having a hollow stem extending from the handle to a leading end, the leading end having a tip portion, the tip portion having a pair of openings for receiving sutures and at least one flat surface extending along the tip portion lengthwise to rotationally fix a bone anchor to the drive shaft;
    a bone anchor having a hollow end opening for attachment on said tip portion, the bone anchor having a first pair of suture openings, the first pair of suture openings being within a thread channel formed by two adjacent threads, the openings of the first pair being within 90 degrees of the other and extending into the hollow end opening;
    a suture threaded and looped through the first pair of suture openings, the suture extending from the bone anchor through one of the openings of the tip portion internally through the hollow stem; and
    wherein the bone anchor has a second pair of openings for receiving a second suture, the second pair being within the thread channel formed by two adjacent threads being similarly spaced relative to the first pair, but on opposite sides of the bone anchor, and the second suture threaded through the second pair of openings and similarly extending from the bone anchor through the opposite opening of the tip portion internally through the hollow stem, wherein only a loop portion of each of the sutures is exposed externally in the thread channel, the exposed loop portion extending 90 degrees or less circumferentially externally around the channel from which the suture is held to the bone anchor.

2. The bone anchor delivery system device of claim 1 wherein the bone anchor has the two pairs of suture openings, each opening of one pair being radially aligned with an opening of another pair.

3. The bone anchor delivery system device of claim 1 wherein the bone anchor has the two pairs of suture openings, each opening of one pair being radially offset relative to the openings of another pair.

4. The bone anchor delivery system device of claim 1 wherein the bone anchor has the two pairs of suture openings, each opening of one pair being linearly aligned with an opening of another pair.

5. The bone anchor delivery system device of claim 1 wherein the bone anchor has the two pairs of suture openings, each opening of one pair being linearly offset relative to the openings of another pair.

6. A bone anchor delivery system device comprises:
    a handle assembly having an upper handle portion and a lower handle portion, the upper and lower handle portions being rotatable relative to the other;
    a bone anchor driver assembly for rotatably driving a bone anchor, the bone anchor driver assembly being fixed to one of said upper or lower handle portions, the driver assembly having an elongated drive shaft fixed to the handle, the drive shaft having a hollow stem extending from the handle to a leading end, the leading end having a tip portion, the tip portion having a pair of openings for receiving sutures and at least one flat surface extending along the tip portion lengthwise to rotationally fix a bone anchor to the drive shaft, the bone anchor having a hollow end opening for attachment on said tip portion, the bone anchor having a first pair of suture openings, the first pair of suture openings being within a thread channel formed by two adjacent threads, the openings of the first pair being within 90 degrees of the other and extending into the hollow end opening, a suture threaded and looped through the first pair of suture openings, the suture extending from the bone anchor through one of the openings of the tip portion internally through the hollow stem, and wherein the bone anchor has a second pair of openings for receiving a second suture, the second pair being within the thread channel formed by two adjacent threads being similarly spaced relative to the first pair, but on opposite sides of the bone anchor, and the second suture threaded through the second pair of openings and similarly extending from the bone anchor through the opposite opening of the tip portion internally through the hollow stem, wherein only a loop portion of each of the sutures is exposed externally in the thread channel, the exposed loop portion extending 90 degrees or less circumferentially externally around the channel from which the suture is held to the bone anchor; and wherein rotation of the handle portion fixed to the driver allows the other handle portion to be held non-rotatably for stabilization of the device.

7. The bone anchor delivery system device of claim 6 wherein the upper handle portion is fixed to the driver assembly.

8. The bone anchor delivery system device of claim 6 wherein the upper handle portion has an impact end for receiving blows from a mallet and the driver assembly has a leading end having the bone anchor positioned on a sharpened metal pointed tip for penetrating bone to form an anchor opening.

9. The bone anchor delivery system device of claim 8 wherein the bone anchor is releasable relative to the driver assembly.

10. The bone anchor delivery system device of claim 9 wherein the bone anchor driver assembly further non-rotatably holds the bone anchor, said bone anchor being releasably held on said driver assembly, and wherein after being driven into said anchor opening, the driver assembly is withdrawn releasing said bone anchor fixed to said bone opening.

11. The bone anchor delivery system device of claim 10 wherein the bone anchor has threads and is rotatably driven into the bone opening.

\* \* \* \* \*